(12) United States Patent  
Ren et al.

(10) Patent No.: US 10,712,315 B2  
(45) Date of Patent: Jul. 14, 2020

(54) DEVICE AND METHOD FOR SUPERVISING BIOFILM CULTURING (71) Applicant: Nanjing University, Nanjing (CN)

(72) Inventors: Hongqiang Ren, Nanjing (CN); Jinfeng Wang, Nanjing (CN); Lili Ding, Nanjing (CN); Jianxin Li, Nanjing (CN); Huimin Fu, Nanjing (CN); Hui Huang, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 179 days.

(21) Appl. No.: 15/871,145

(22) Filed: Jan. 15, 2018

(65) Prior Publication Data

US 2018/0136168 A1    May 17, 2018

Related U.S. Application Data

(63) Continuation-in-part of application No. PCT/CN2017/095850, filed on Aug. 3, 2017.

(30) Foreign Application Priority Data

Nov. 9, 2016    (CN) .......................... 2016 1 0984895

(51) Int. Cl.  
*G01N 33/487*    (2006.01)  
*C02F 3/00*      (2006.01)  
(Continued)

(52) U.S. Cl.  
CPC ........... *G01N 29/036* (2013.01); *C02F 3/006* (2013.01); *C02F 3/12* (2013.01); *G01N 29/222* (2013.01);  
(Continued)

(58) Field of Classification Search  
CPC .. G01N 29/036; G01N 33/487; G01N 29/348; G01N 29/223; G01N 29/222;  
(Continued)

(56) References Cited

U.S. PATENT DOCUMENTS 3,570,302 A * 3/1971 Sauer ..................... G01N 25/18  
374/43  
5,349,874 A * 9/1994 Schapira ................ G01N 17/00  
73/86

(Continued)

*Primary Examiner* — Jacques M Saint Surin  
(74) *Attorney, Agent, or Firm* — Matthias Scholl P.C.; Matthias Scholl (57) ABSTRACT

A device for supervising biofilm culturing, the device including: a fixed seat including an upper end; a supervision chamber; two ultrasonic sensing probes; a first mounting chamber; a second mounting chamber disposed between the fixed seat and the supervision chamber; an ultrasonic generator; an oscilloscope; and a controller. The first and second mounting chambers are disposed at two opposite ends of the supervision chamber, respectively. The two ultrasonic sensing probes are disposed in the first and second mounting chambers, respectively. The second mounting chamber is connected to the upper end of the fixed seat. The two ultrasonic sensing probes each are respectively connected to the ultrasonic generator, the oscilloscope, and the controller successively.

9 Claims, 5 Drawing Sheets

(51) Int. Cl.
  *G01N 29/34* (2006.01)
  *C02F 3/12* (2006.01)
  *G01N 29/22* (2006.01)
  *G01N 29/036* (2006.01)

(52) U.S. Cl.
  CPC ......... *G01N 29/223* (2013.01); *G01N 29/348* (2013.01); *G01N 33/487* (2013.01); *G01N 2291/0228* (2013.01); *G01N 2291/0255* (2013.01)

(58) Field of Classification Search
  CPC .... G01N 2291/0255; G01N 2291/0228; C02F 3/006; C02F 3/12
  USPC .......................................................... 73/644
  See application file for complete search history.

(56) References Cited

U.S. PATENT DOCUMENTS

| | | | | |
|---|---|---|---|---|
| 5,488,856 A | * | 2/1996 | Dirk ................... | G01N 33/1866 73/61.41 |
| 2010/0206079 A1 | * | 8/2010 | Vlahopoulou ......... | C12M 41/36 73/599 |

* cited by examiner

FIG. 3B

DEVICE AND METHOD FOR SUPERVISING BIOFILM CULTURING

CROSS-REFERENCE TO RELAYED APPLICATIONS

This application is a continuation-in-part of International Patent Application No. PCT/CN2017/095850 with an international filing date of Aug. 3, 2017, designating the United States, now pending, and further claims foreign priority benefits to Chinese Patent Application No. 201610984895.6 filed Nov. 9, 2016. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, Cambridge, Mass. 02142.

BACKGROUND OF THE INVENTION

Field of the Invention

The disclosure relates to a device and method for supervising biofilm culturing.

Description of the Related Art

In the present, biofilms are widely used for sewage treatment. However, subject to the complexity of water bodies and the variety of the bacteria in the sludge, the biofilm culturing performance of the fillers in different water bodies varies greatly. Conventionally, the fillers are directly added to a water body for biofilm culturing. The biofilm culturing process is laborious, time-consuming, and is likely to fail.

SUMMARY OF THE INVENTION

In view of the above-described problems, it is one objective of the invention to provide a device and method for supervising biofilm culturing that is effective and efficient in matching a filler and a target water body for biofilm culturing for sewage treatment.

To achieve the above objectives, in accordance with one embodiment of the invention, there is provided a device for supervising biofilm culturing, the device comprising: a fixed seat comprising an upper end; a supervision chamber; two ultrasonic sensing probes; a first mounting chamber; a second mounting chamber disposed between the fixed seat and the supervision chamber; an ultrasonic generator; an oscilloscope; and a controller. The first and second mounting chambers are disposed at two opposite ends of the supervision chamber, respectively; the two ultrasonic sensing probes are disposed in the first and second mounting chambers, respectively; the second mounting chamber is connected to the upper end of the fixed seat; and the two ultrasonic sensing probes each are respectively connected to the ultrasonic generator, the oscilloscope, and the controller successively.

In a class of this embodiment, the fixed seat comprises a circular pedestal and a semi-open cylinder.

In a class of this embodiment, the supervision chamber is transparent and comprises a side wall and a bottom wall; the side wall comprises a water inlet and a water outlet which is located higher than the water inlet; and the bottom wall comprises a groove for receiving a filler film.

In a class of this embodiment, the first mounting chamber is disposed on the supervision chamber; the first mounting chamber comprises a cylindrical holder and a chamber for accommodating one of the two ultrasonic sensing probes; the chamber for accommodating the one of the two ultrasonic sensing probes is disposed on an upper surface of the cylindrical holder; a first fixation device is disposed in the chamber to fix the one of the two ultrasonic sensing probes; the one of the two ultrasonic sensing probes is fixed on a side wall of the first fixation device; the cylindrical holder comprises a side wall and a plurality of slots disposed on the side wall; the slots correspond to the water inlet and the water outlet of the supervision chamber; the second mounting chamber comprises a second fixation device for accommodating the other of the two ultrasonic sensing probes; and the other of the two ultrasonic sensing probes is fixed on a side wall of the second fixation device.

In a class of this embodiment, the two ultrasonic sensing probes are coated with a coupling agent and then fixed on sides wall of the first and second fixation devices.

In a class of this embodiment, the cylindrical holder of the first mounting chamber comprises a bottom edge, and an annular groove and a gasket are disposed on the bottom edge; the first mounting chamber and the supervision chamber are fixed and sealed using the annular groove and the gasket.

In another aspect, the disclosure provides a method for supervising biofilm culturing, the method comprising:
1) sampling a mixture of target muddy water, and homogenizing the mixture;
2) filtering the homogenized mixture of muddy water, and collecting a filtrate resulting therefrom;
3) dividing the filtrate into two parts, labeling one of the two parts as Filtrate A; filtering the other part of the two parts using a filter membrane to yield another filtrate which is labeled as Filtrate B;
4) assembling the device for supervising biofilm culturing of claim;
5) fixing a first filler film in the supervision chamber;
6) pumping the Filtrate A into the supervision chamber via a water inlet thereof;
7) starting the ultrasonic generator when the Filtrate A is about to overflow from a water outlet of the supervision chamber, turning on an ultrasonic reflection mode, adjusting working parameters of the ultrasonic generator to preset values, opening the oscilloscope, and on-line supervising the biofilm culturing on the first filler film through the controller;
8) substituting the Filtrate B for the Filtrate A, and repeating 6)-7);
9) recording a time with regard to the biofilm culturing on the first filler film according to an oscillogram on the oscilloscope;
10) replacing the first filler film using a second filler film, repeating 5)-9), and recording a time with regard to the biofilm culturing on the second filler film; and
11) based on the observation results in 9-10), selecting a filler with which the biofilm culturing is the quickest to use in a target water body for sewage treatment.

In a class of this embodiment, in 1), the mixture is homogenized for 10-15 times.

In a class of this embodiment, in 2), the homogenized mixture of muddy water is filtered using an 8-10 μm filter membrane; in 3), the other part of the two parts is filtered using a 0.22-0.45 μm filter membrane.

In a class of this embodiment, in 6), a flow rate of the Filtrate A into the supervision chamber is 0.5-10 mL/min.

In a class of this embodiment, in 7), the working parameters of the ultrasonic generator 9 are as follows: repetition frequency, 15-25 Hz; pulse resistance, 30-60Ω; pulse voltage, 200-400 V; gain, 60 dB; high-pass filtering, 0.03-0.1 mHz; and low-pass filtering, 1-3 mHz.

Advantages of the device and method for supervising biofilm culturing of the disclosure are summarized as follows.

1. Through the device of the disclosure, different water bodies and fillers are employed to perform matching experiments, and based on the experimental results to select optimal filler for biofilm culturing. So, there is no need to develop special membranes for special water bodies, saving the resources and reducing the costs.

2. The device for supervising biofilm culturing of the disclosure comprises a main body, a built-in cylinder, ultrasonic sensing probes, a signal generator, an oscilloscope, and a controller, so it is simple, easy to install and operate.

3. The supervision chamber is transparent and comprises two mounting chambers for accommodating filler films, the filler films are easy to replace, so the experimental operation is efficient.

4. The two ultrasonic sensing probes are coated with a coupling agent and then fixed on sides wall of the first and second fixation devices using the screws, which greatly improves the accuracy of ultrasonic detection.

5. The basic operation process of the method is: pretreatment of sludge—installation of filler film—on-line supervision of the biofilm culturing on the first filler film—selection of a filler with which the biofilm culturing is the quickest to use in a target water body for sewage treatment. The method of the disclosure aims at finding an optimum matching of a filler and a water body, no need to develop special membranes for special water bodies, saving the resources and reducing the costs. The monitoring device is an on-line, non-contact and real-time non-destructive monitoring system. The monitoring is timesaving, efficient, accurate, inexpensive, safe and environmentally friendly.

6. The detection device of the invention is connected to an oscilloscope and controller, which can observe the data directly. It is on online, real-time, non-contact, direct, and non-destructive detection, with short detection time and high efficiency.

7. The device has good matching accuracy, low cost, and safe operation, can greatly save the space and time of different biofilm culturing tests in different water bodies, and provides reliable biofilm culturing schemes for difficult water bodies.

BRIEF DESCRIPTION OF THE DRAWINGS

The invention is described hereinbelow with reference to the accompanying drawings, in which.

In the drawings, the following reference numbers are used: 1. fixed seat; 2. first mounting chamber; 2'. second mounting chamber; 3. Filler film; 4. Supervision chamber; 5. Water inlet; 6. Water outlet; 7. Ultrasonic sensing probe; 8. Screw; 9. Ultrasonic generator; 10. Oscilloscope; 11. Controller.

DETAILED DESCRIPTION OF THE EMBODIMENTS

For further illustrating the invention, experiments detailing a device and method for supervising biofilm culturing are described below.

Figure 1:
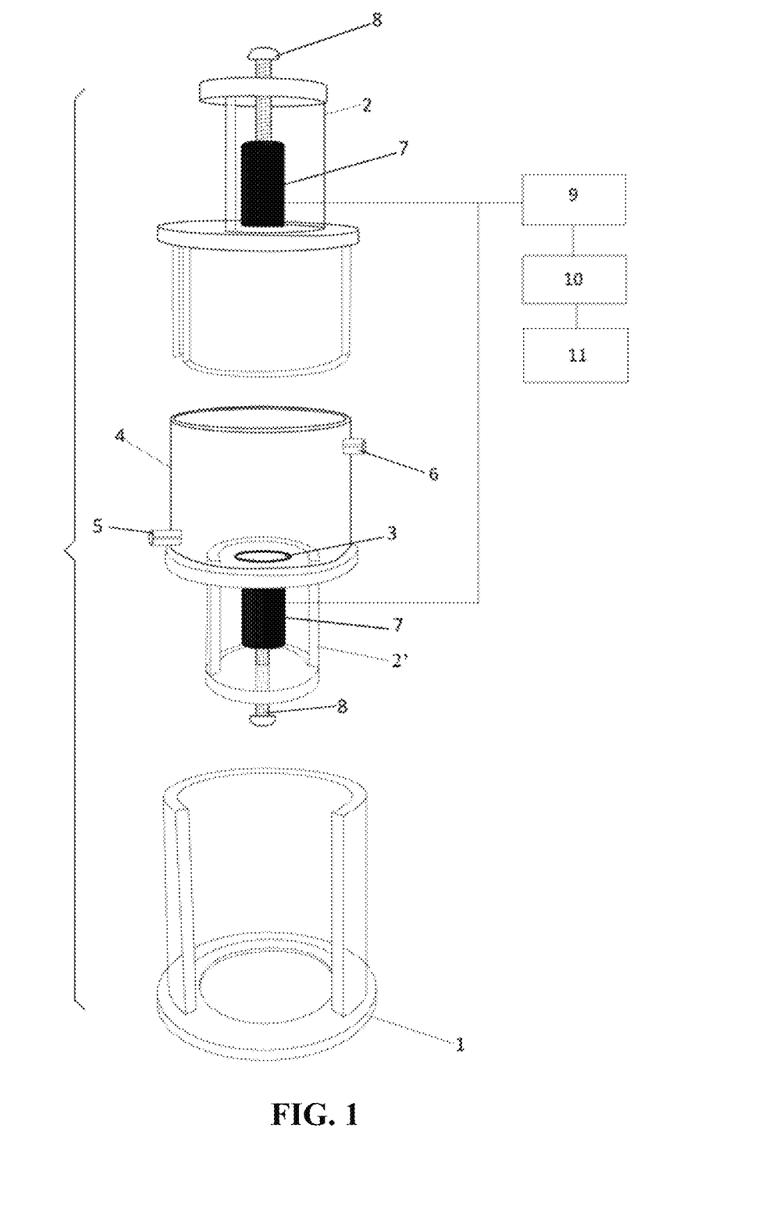
FIG. 1 is an exploded view of a device for supervising biofilm culturing in accordance with one embodiment of the disclosure.
Figure 2A:
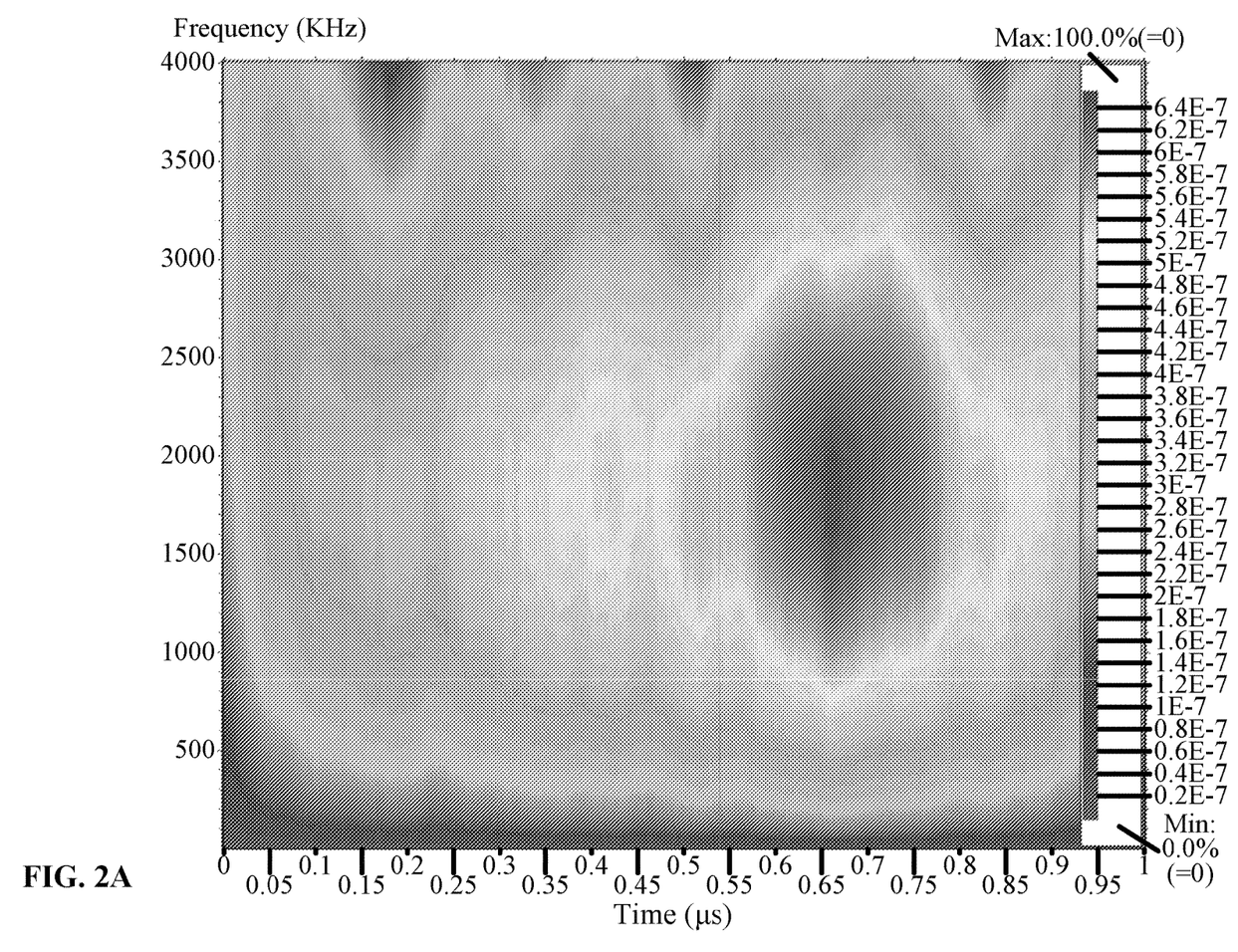
FIG. 2A is a signal image of a first filler prior to biofilm culturing.
Figure 2B:
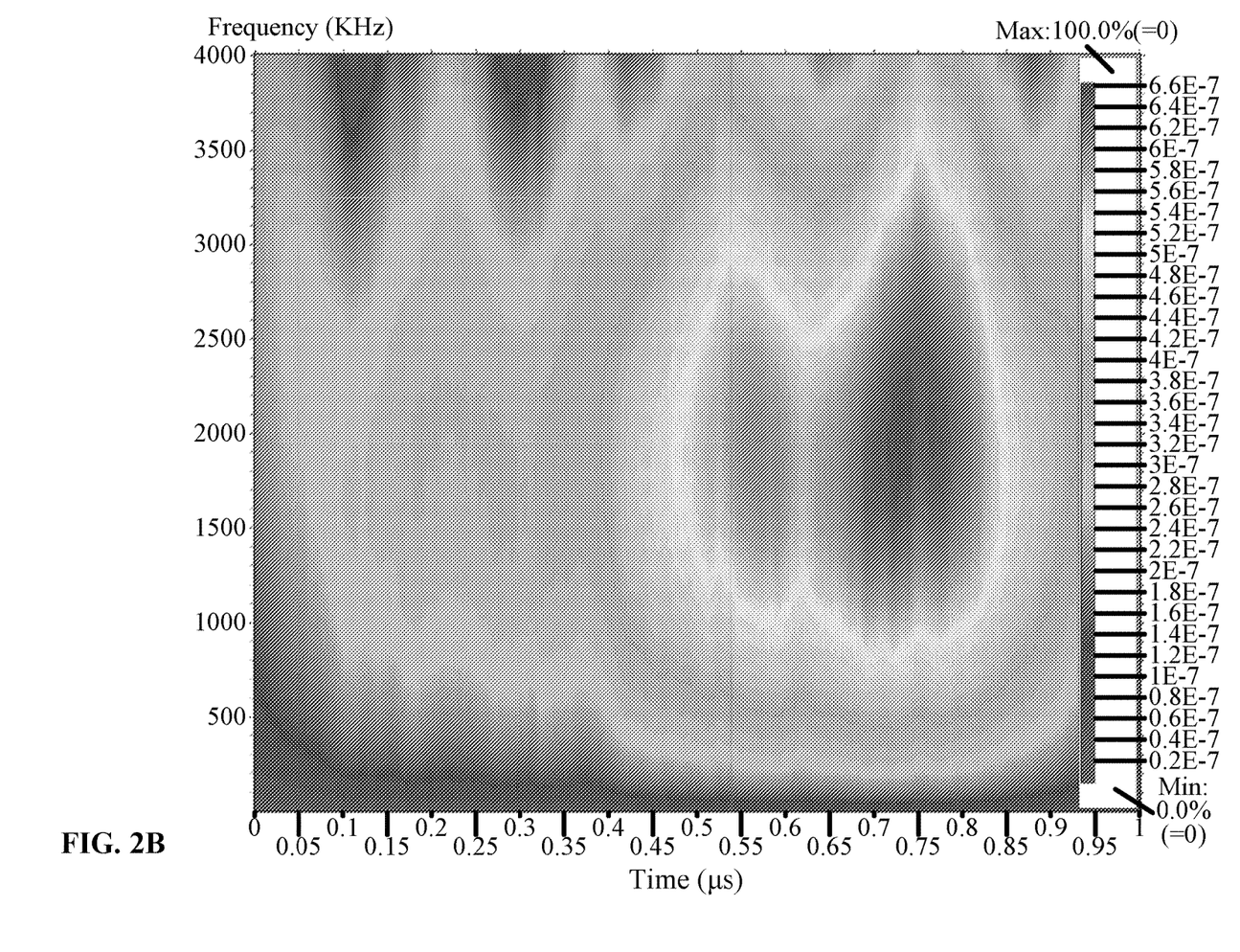
FIG. 2B is a signal image of the first filler after 8 hours' biofilm culturing.

As shown in FIG. 1, a device for supervising biofilm culturing, comprises: a fixed seat 1 comprising an upper end; a supervision chamber 4; two ultrasonic sensing probes 7; a first mounting chamber 2; a second mounting chamber 2' disposed between the fixed seat 1 and the supervision chamber 4; an ultrasonic generator 9; an oscilloscope 10; and a controller 11. The fixed seat 1 comprises a circular pedestal and a semi-open cylinder.

The supervision chamber 4 is transparent and comprises a side wall and a bottom wall; the side wall comprises a water inlet 5 and a water outlet 6 which is located higher than the water inlet 5; and the bottom wall comprises a groove for receiving a filler film 3.

The first and second mounting chambers are disposed at two opposite ends of the supervision chamber 4, respectively; the two ultrasonic sensing probes 7 are disposed in the first and second mounting chambers, respectively; the second mounting chamber 2' is connected to the upper end of the fixed seat 1; and the two ultrasonic sensing probes 7 each are respectively connected to the ultrasonic generator 9, the oscilloscope 10, and the controller 11 successively. The first mounting chamber 2 is disposed on the supervision chamber 4; the first mounting chamber 2 comprises a cylindrical holder and a chamber for accommodating one of the two ultrasonic sensing probes 7; the chamber for accommodating the one of the two ultrasonic sensing probes is disposed on an upper surface of the cylindrical holder; a first fixation device is disposed in the chamber to fix the one of the two ultrasonic sensing probes; the one of the two ultrasonic sensing probes is fixed on a side wall of the first fixation device using screws 8; the cylindrical holder comprises a side wall and a plurality of slots disposed on the side wall; the slots correspond to the water inlet 5 and the water outlet 6 of the supervision chamber 4; the second mounting chamber 2' comprises a second fixation device for accommodating the other of the two ultrasonic sensing probes 7; and the other of the two ultrasonic sensing probes is fixed on a side wall of the second fixation device using screws 8. The two ultrasonic sensing probes 7 are coated with a coupling agent and then fixed on sides wall of the first and second fixation devices using the screws 8. The device has the advantages of simple structure, high work efficiency, and is easy to assemble and operate.

A method for supervising biofilm culturing using the device, comprises:

1) sampling a mixture of target muddy water, and homogenizing the mixture;
2) filtering the homogenized mixture of muddy water, and collecting a filtrate resulting therefrom;
3) dividing the filtrate into two parts, labeling one of the two parts as Filtrate A; filtering the other part of the two parts using a filter membrane to yield another filtrate which is labeled as Filtrate B;
4) assembling the device for supervising biofilm culturing of claim 1;
5) fixing a first filler film 3 in the supervision chamber 4;

6) pumping the Filtrate A into the supervision chamber 4 via a water inlet 5 thereof;

7) starting the ultrasonic generator 9 when the Filtrate A is about to overflow from a water outlet of the supervision chamber 4, turning on an ultrasonic reflection mode, adjusting working parameters of the ultrasonic generator 9 to preset values, opening the oscilloscope 10, and on-line supervising the biofilm culturing on the first filler film through the controller 11;

8) substituting the Filtrate B for the Filtrate A, and repeating 6)-7);

9) recording a time with regard to the biofilm culturing on the first filler film according to an oscillogram on the oscilloscope 10;

10) replacing the first filler film using a second filler film, repeating 5)-9), and recording a time with regard to the biofilm culturing on the second filler film; and 11) based on the observation results in 9-10), selecting a filler with which the biofilm culturing is the quickest to use in a target water body for sewage treatment.

More other fillers made of different materials can be used for the test of biofilm culturing, which is conducive to selecting an optimum filler for sewage treatment.

Example 1

The effluent quality of an industrial wastewater does not fulfill the emission standard, so the disclosure proposes a biofilm method to upgrade the sewage treatment of the original aerobic tank.

Specifically, the method comprises:

1) sampling a mixture of target muddy water, and homogenizing the mixture for 15 times;

2) filtering the homogenized mixture of muddy water using a 10 μm filter membrane, and collecting a filtrate resulting therefrom;

3) dividing the filtrate into two parts, labeling one of the two parts as Filtrate A; filtering the other part of the two parts using a 0.22 μm filter membrane to yield another filtrate which is labeled as Filtrate B;

4) assembling the device for supervising biofilm culturing;

5) fixing a first filler film 3 in the supervision chamber 4;

6) pumping the Filtrate A into the supervision chamber 4 via a water inlet 5 thereof, the flow rate of the Filtrate A into the supervision chamber 4 is 1 mL/min;

7) starting the ultrasonic generator 9 when the Filtrate A is about to overflow from a water outlet of the supervision chamber 4, turning on an ultrasonic reflection mode, adjusting working parameters of the ultrasonic generator 9 to preset values, opening the oscilloscope 10, and on-line supervising the biofilm culturing on the first filler film through the controller 11; where the working parameters of the ultrasonic generator 9 are as follows: repetition frequency, 20 Hz; pulse resistance, 30Ω; pulse voltage, 400 V; gain, 60 dB; high-pass filtering, 0.03 mHz; and low-pass filtering, 1 mHz;

8) substituting the Filtrate B for the Filtrate A, and repeating 6)-7);

9) recording a time with regard to the biofilm culturing on the first filler film according to an oscillogram on the oscilloscope 10;

10) replacing the first filler film using a second filler film, repeating 5)-9), and recording a time with regard to the biofilm culturing on the second filler film; and 11) based on the observation results in 9-10), selecting a filler with which the biofilm culturing is the quickest to use in a target water body for sewage treatment.

Figure 3A:
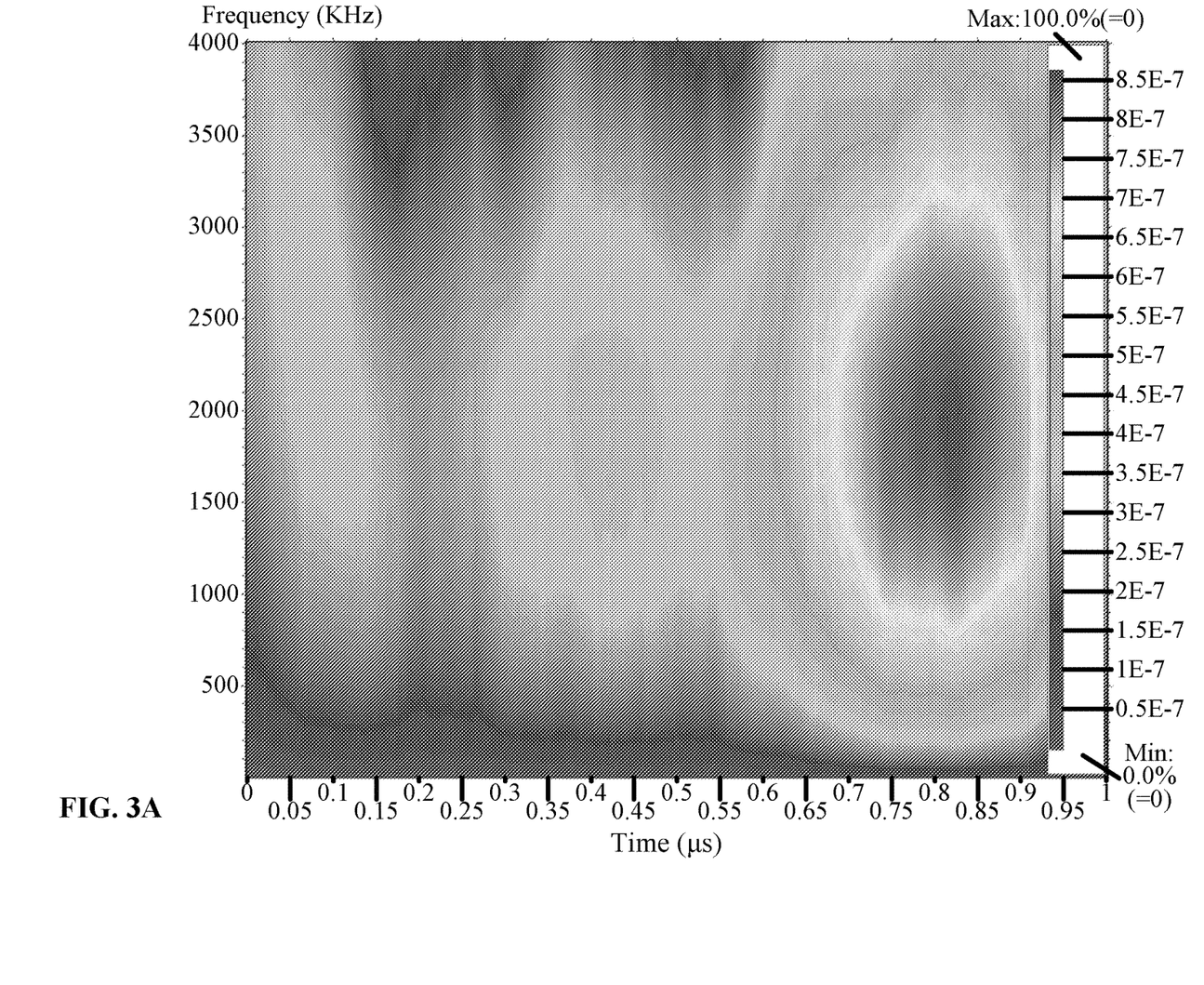
FIG. 3A is a signal image of a second filler prior to biofilm culturing.
Figure 3B:
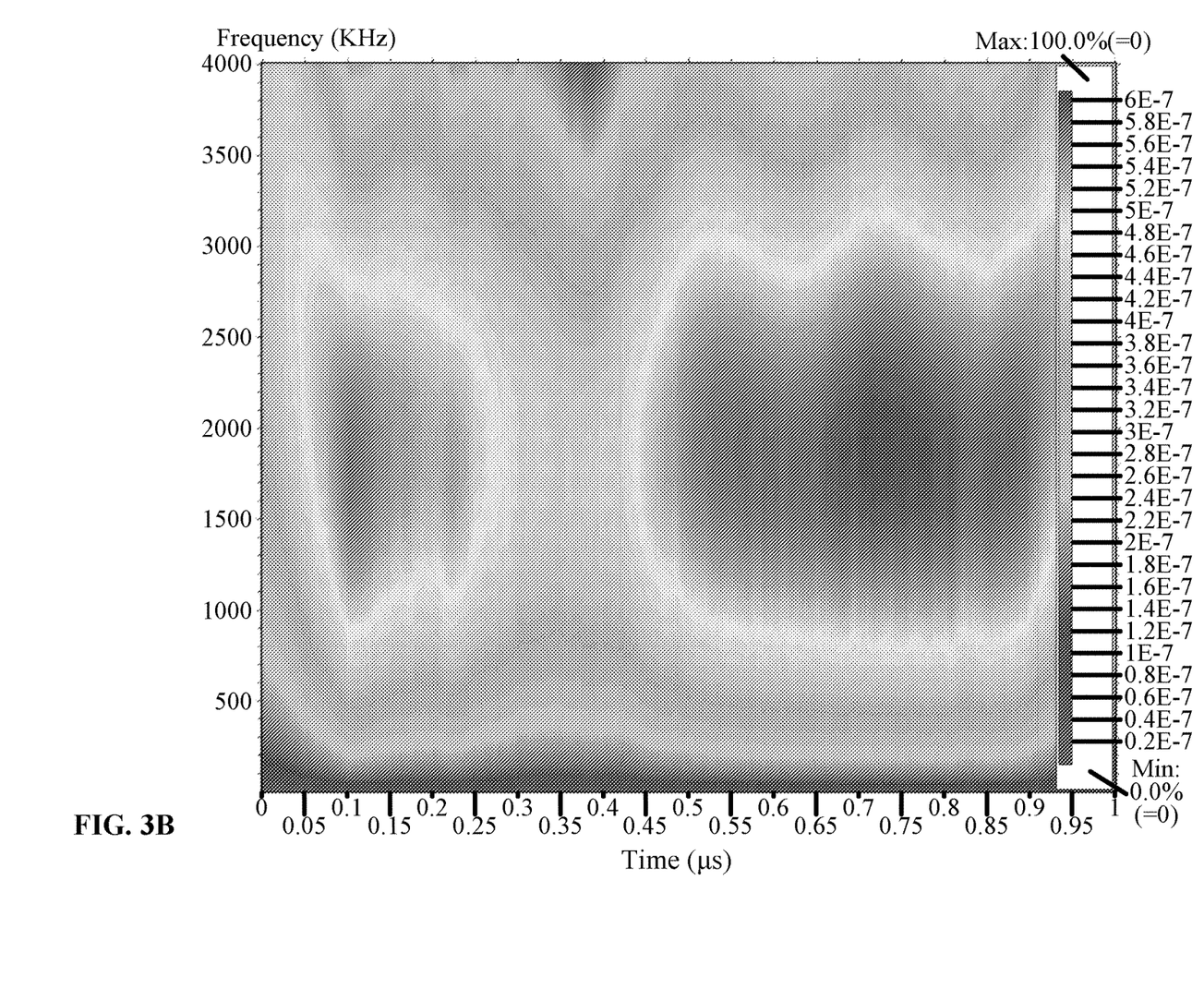
FIG. 3B is a signal image of the second filler after 8 hours' biofilm culturing.

As shown in FIGS. 2A, 2B, 3A, and 3B, it is known that besides the signal corresponding to the deposition of inorganic salts at 0.45 μs and the echoed signal of the filler at 0.85 μs, in FIG. 3B, after 8 hours' biofilm culturing, the echoed signal of the formation of biofilm on the filler is firstly captured at 0.1 μs. Experimental results in this example show that the filler corresponding to the second filler film is suitable for biofilm culturing in the target water body.

Example 2

The effluent quality of an industrial wastewater does not fulfill the emission standard, so the disclosure proposes a biofilm method to upgrade the sewage treatment of the original aerobic tank.

Specifically, the method comprises:

1) sampling a mixture of target muddy water, and homogenizing the mixture for 10 times;

2) filtering the homogenized mixture of muddy water using an 8 μm filter membrane, and collecting a filtrate resulting therefrom;

3) dividing the filtrate into two parts, labeling one of the two parts as Filtrate A; filtering the other part of the two parts using a 0.45 μm filter membrane to yield another filtrate which is labeled as Filtrate B;

4) assembling the device for supervising biofilm culturing;

5) fixing a first filler film 3 in the supervision chamber 4;

6) pumping the Filtrate A into the supervision chamber 4 via a water inlet 5 thereof, the flow rate of the Filtrate A into the supervision chamber 4 is 10 mL/min;

7) starting the ultrasonic generator 9 when the Filtrate A is about to overflow from a water outlet of the supervision chamber 4, turning on an ultrasonic reflection mode, adjusting working parameters of the ultrasonic generator 9 to preset values, opening the oscilloscope 10, and on-line supervising the biofilm culturing on the first filler film through the controller 11; where the working parameters of the ultrasonic generator 9 are as follows: repetition frequency, 15 Hz; pulse resistance, 60Ω; pulse voltage, 200 V; gain, 60 dB; high-pass filtering, 0.1 mHz; and low-pass filtering, 3 mHz;

8) substituting the Filtrate B for the Filtrate A, and repeating 6)-7);

9) recording a time with regard to the biofilm culturing on the first filler film according to an oscillogram on the oscilloscope 10;

10) replacing the first filler film using a second filler film, repeating 5)-9), and recording a time with regard to the biofilm culturing on the second filler film; and 11) based on the observation results in 9-10), selecting a filler with which the biofilm culturing is the quickest to use in a target water body for sewage treatment.

Example 3

The effluent quality of an industrial wastewater does not fulfill the emission standard, so the disclosure proposes a biofilm method to upgrade the sewage treatment of the original aerobic tank.

Specifically, the method comprises:

1) sampling a mixture of target muddy water, and homogenizing the mixture for 12 times;

2) filtering the homogenized mixture of muddy water using a 9 μm filter membrane, and collecting a filtrate resulting therefrom;

3) dividing the filtrate into two parts, labeling one of the two parts as Filtrate A; filtering the other part of the two parts using a 0.3 μm filter membrane to yield another filtrate which is labeled as Filtrate B;

4) assembling the device for supervising biofilm culturing;

5) fixing a first filler film 3 in the supervision chamber 4;

6) pumping the Filtrate A into the supervision chamber 4 via a water inlet 5 thereof, the flow rate of the Filtrate A into the supervision chamber 4 is 0.5 mL/min;

7) starting the ultrasonic generator 9 when the Filtrate A is about to overflow from a water outlet of the supervision chamber 4, turning on an ultrasonic reflection mode, adjusting working parameters of the ultrasonic generator 9 to preset values, opening the oscilloscope 10, and on-line supervising the biofilm culturing on the first filler film through the controller 11; where the working parameters of the ultrasonic generator 9 are as follows: repetition frequency, 25 Hz; pulse resistance, 40Ω; pulse voltage, 300 V; gain, 60 dB; high-pass filtering, 0.05 mHz; and low-pass filtering, 2 mHz;

8) substituting the Filtrate B for the Filtrate A, and repeating 6)-7);

9) recording a time with regard to the biofilm culturing on the first filler film according to an oscillogram on the oscilloscope 10;

10) replacing the first filler film using a second filler film, repeating 5)-9), and recording a time with regard to the biofilm culturing on the second filler film; and 11) based on the observation results in 9-10), selecting a filler with which the biofilm culturing is the quickest to use in a target water body for sewage treatment.

Example 4

The effluent quality of an industrial wastewater does not fulfill the emission standard, so the disclosure proposes a biofilm method to upgrade the sewage treatment of the original aerobic tank.

Specifically, the method comprises:

1) sampling a mixture of target muddy water, and homogenizing the mixture for 12 times;

2) filtering the homogenized mixture of muddy water using a 9 μm filter membrane, and collecting a filtrate resulting therefrom;

3) dividing the filtrate into two parts, labeling one of the two parts as Filtrate A; filtering the other part of the two parts using a 0.3 μm filter membrane to yield another filtrate which is labeled as Filtrate B;

4) assembling the device for supervising biofilm culturing;

5) fixing a first filler film 3 in the supervision chamber 4;

6) pumping the Filtrate A into the supervision chamber 4 via a water inlet 5 thereof, the flow rate of the Filtrate A into the supervision chamber 4 is 0.5 mL/min;

7) starting the ultrasonic generator 9 when the Filtrate A is about to overflow from a water outlet of the supervision chamber 4, turning on an ultrasonic reflection mode, adjusting working parameters of the ultrasonic generator 9 to preset values, opening the oscilloscope 10, and on-line supervising the biofilm culturing on the first filler film through the controller 11; where the working parameters of the ultrasonic generator 9 are as follows: repetition frequency, 25 Hz; pulse resistance, 40Ω; pulse voltage, 300 V; gain, 60 dB; high-pass filtering, 0.05 mHz; and low-pass filtering, 2 mHz;

8) substituting the Filtrate B for the Filtrate A, and repeating 6)-7);

9) recording a time with regard to the biofilm culturing on the first filler film according to an oscillogram on the oscilloscope 10;

10) replacing the first filler film using a second filler film, repeating 5)-9), and recording a time with regard to the biofilm culturing on the second filler film; and 11) based on the observation results in 9-10), selecting a filler with which the biofilm culturing is the quickest to use in a target water body for sewage treatment.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for supervising biofilm culturing, the device comprising:
 a fixed seat comprising an upper end;
 a supervision chamber;
 two ultrasonic sensing probes;
 a first mounting chamber;
 a second mounting chamber disposed between the fixed seat and the supervision chamber;
 an ultrasonic generator;
 an oscilloscope; and
 a controller;
wherein:
 the first and second mounting chambers are disposed at two opposite ends of the supervision chamber, respectively;
 the two ultrasonic sensing probes are disposed in the first and second mounting chambers, respectively;
 the second mounting chamber is connected to the upper end of the fixed seat;
 each of the two ultrasonic sensing probes is connected to the ultrasonic generator, the oscilloscope, and the controller successively;
 the supervision chamber is transparent and comprises a side wall and a bottom wall; the side wall comprises a water inlet and a water outlet which is located higher than the water inlet and the bottom wall comprises a groove for receiving a filler film; and
 the first mounting chamber is disposed on the supervision chamber; the first mounting chamber comprises a cylindrical holder and a chamber for accommodating one of the two ultrasonic sensing probes; the chamber for accommodating the one of the two ultrasonic sensing probes is disposed on an upper surface of the cylindrical holder; a first fixation device is disposed in the chamber to fix the one of the two ultrasonic sensing probes; the one of the two ultrasonic sensing probes is fixed on a side wall of the first fixation device; the cylindrical holder comprises a holder side wall and a plurality of slots disposed on the holder side wall; the slots correspond to the water inlet and the water outlet of the supervision chamber; the second mounting chamber comprises a second fixation device for accommodating the other of the two ultrasonic sensing probes; and the other of the two ultrasonic sensing probes is fixed on a side wall of the second fixation device.

2. The device of claim 1, wherein the fixed seat comprises a circular pedestal and a semi-open cylinder.

3. The device of claim 1, wherein the two ultrasonic sensing probes are coated with a coupling agent.

4. The device of claim 1, wherein the cylindrical holder of the first mounting chamber comprises a bottom edge, and an annular groove, and a gasket the annular groove and the gasket are disposed on the bottom edge; and the first mounting chamber and the supervision chamber are fixed and sealed using the annular groove and the gasket.

5. A method for supervising biofilm culturing, the method comprising:
1) sampling a mixture of target muddy water, and homogenizing the mixture;
2) filtering the homogenized mixture of muddy water, and collecting a filtrate resulting therefrom;
3) dividing the filtrate into two parts, labeling one of the two parts as Filtrate A; filtering the other part of the two parts using a filter membrane to yield another filtrate which is labeled as Filtrate B;
4) assembling the device for supervising biofilm culturing of claim 1;
5) fixing a first filler film in the supervision chamber;
6) pumping the Filtrate A into the supervision chamber via the water inlet thereof;
7) starting the ultrasonic generator when the Filtrate A is about to overflow from the water outlet of the supervision chamber, turning on an ultrasonic reflection mode, adjusting working parameters of the ultrasonic generator to preset values, opening the oscilloscope, and on-line supervising the biofilm culturing on the first filler film through the controller;
8) substituting the Filtrate B for the Filtrate A, and repeating 6)-7);
9) recording a time with regard to the biofilm culturing on the first filler film according to an oscillogram on the oscilloscope;
10) replacing the first filler film using a second filler film, repeating 5)-9); and
11) based on the observation results in 9), selecting a filler with which the biofilm culturing is the quickest to use in a target water body for sewage treatment.

6. The method of claim 5, wherein in 1), the mixture is homogenized for 10-15 times.

7. The method of claim 5, wherein in 2), the homogenized mixture of muddy water is filtered using an 8-10 µm filter membrane; in 3), the other part of the two parts is filtered using a 0.22-0.45 µm filter membrane.

8. The method of claim 5, wherein in 6), a flow rate of the Filtrate A into the supervision chamber is 0.5-10 mL/min.

9. The method of claim 5, wherein in 7), the working parameters of the ultrasonic generator are as follows: repetition frequency, 15-25 Hz; pulse resistance, 30-60Ω; pulse voltage, 200-400 V; gain, 60 dB; high-pass filtering, 0.03-0.1 mHz; and low-pass filtering, 1-3 mHz.

* * * * *